(12) United States Patent
Heumann et al.

(10) Patent No.: US 6,850,589 B2
(45) Date of Patent: Feb. 1, 2005

(54) TOMOGRAPHY OF CURVED SURFACES

(75) Inventors: John M. Heumann, Loveland, CO (US); David C. Reynolds, Loveland, CO (US)

(73) Assignee: Agilent Technologies, Inc., Palo Alto, CA (US)

(*) Notice: Subject to any disclaimer, the term of this patent is extended or adjusted under 35 U.S.C. 154(b) by 193 days.

(21) Appl. No.: 10/107,562

(22) Filed: Mar. 27, 2002

(65) Prior Publication Data

US 2003/0185339 A1 Oct. 2, 2003

(51) Int. Cl.$^7$ .............................................. H05G 1/32
(52) U.S. Cl. ..................................... 378/19; 378/21
(58) Field of Search ............................. 378/19, 21–27, 378/98.8, 4; 250/363.04, 363.07, 363.08, 363.09, 366

(56) References Cited

U.S. PATENT DOCUMENTS

| | | | |
|---|---|---|---|
| 5,081,656 A | | 1/1992 | Baker et al. |
| 5,319,693 A | * | 6/1994 | Eberhard et al. ............. 378/19 |
| 5,524,038 A | | 6/1996 | Fong |
| 5,606,167 A | * | 2/1997 | Miller ................... 250/390.04 |
| 5,687,209 A | | 11/1997 | Adams |
| 5,740,224 A | * | 4/1998 | Muller et al. ................. 378/11 |
| 5,757,006 A | * | 5/1998 | DeVito et al. ............. 250/366 |
| 5,825,841 A | * | 10/1998 | Timmer ......................... 378/4 |
| 6,201,850 B1 | | 3/2001 | Heumann |
| 6,285,028 B1 | * | 9/2001 | Yamakawa ............. 250/370.09 |

FOREIGN PATENT DOCUMENTS

JP 52030395 3/1977

OTHER PUBLICATIONS

D. Grant, "Tomosynthesis: A Three–Dimensional Radiographic Imaging Technique," IEEE Trans. Biomed. Eng: BME: 19: 20–28, (1972).

J. Liu, D. Nishimura, A. Macovski, "Vessel Imaging Using Dual Energy Tomosynthesis," Med. Phys. 14(6): 950–955 (1987).

Z. Kolitsi, G. Panayiotakis, V. Anastassopoulos, A. Scodras, N. Pallikarakis, "A Multiple Projection Method for Digital Tomosynthesis," Med. Phys. 19(4): 1045–1050 (1992).

L. Yaroslavsky, "Advanced Image Processing Lab," European Signal Processing Conference 2000, (Tampere, Finland, Sep. 4, 2000).

T. Smith, M. Smith, S. Nichols, "Efficient Sinc Function Interpolation Technique for Center Padded Data," IEEE Trans. Acoust. Speech Signal Proc. 38:1512–1517 (1990).

L.P. Yaroslavsky, "Efficient Algorithm for Discrete Sinc Interpolation," Applied Optics, 36(2): 460–463 (1997).

* cited by examiner

Primary Examiner—Edward J. Glick
Assistant Examiner—Hoon Song

(57) ABSTRACT

Disclosed are a method and apparatus for tomography of a curved surface in an object. One embodiment is a method that includes determining an expected distortion for each of a plurality of points in a projection of the curved surface, and correcting each of the plurality of points in the projection according to the expected distortion of that point by replacing pixel values in the uncorrected projection with corresponding interpolated pixel values at the expected positions.

34 Claims, 12 Drawing Sheets

```
pro warp n = 256;         N MUST BE EVEN, >= 16 while (!d.window ne -1) do wdelete;

; define warped surface at origin
step = fix(n/16);
zo = shift(dist(n, n), n/2, n/2) * 8 * !pi / (n * sqrt(2));
zo = 25*sin(zo)/zo;
window, 0, xsize=n, ysize=n, title='Warped Surface'
shade_surf, zo;

xo = dblarr(n, n);
yo = dblarr(n, n);
obj = bytarr(n, n);
for i = 0, n - 1 do begin
    xo[i, *] = i - n/2 + 0.5;
    yo[*, i] = i - n/2 + 0.5;
endfor;
for i = step, n - step, step do begin
    obj[i, step:n-step] = 255;
    obj[step:n-step, i] = 255;
endfor;
ndx = where(obj ne 0);   Remember non-zero positions ; mesh representation of original surface
zm=dblarr(n/16, n/16);
xm=dblarr(n/16, n/16);
ym=dblarr(n/16, n/16);
for i = 0, n / 16 - 1 do begin
    for j = 0, n / 16 - 1 do begin
        xm[i, j] = xo[16 * i, 16 * j];
        ym[i, j] = yo[16 * i, 16 * j];
        zm[i, j] = zo[16 * i, 16 * j];
    endfor;
endfor;
window, 1, xsize=n, ysize=n, title='Warped Surface'
surface, zm, xm, ym;

; display the original object
window, 2, xsize=n, ysize=n, title='Flat Object'
tv, obj;

; define source position
zs = 1000;
xs = 707;
ys = 707;

; define flat detector pixel array
zd0 = dblarr(n, n) - 9000;
mag0 = (-9000 - zs) / (-zs);   Flat object to flat detector
x0 = xs + mag0 * (xo - xs);
xc0 = xs - mag0 * xs;
y0 = ys + mag0 * (yo - ys);
yc0 = ys - mag0 * ys;
ix = floor((x0 - xc0) / mag0 + n / 2);
```

FIG. 8A

```
        iy = floor((y0 - yc0) / mag0 + n / 2);
        img = bytarr(n, n);
        img[ix[ndx], iy[ndx]] = obj[ndx];
        window, 3, xsize=n, ysize=n, title='Flat Obj/ Flat Det'
 5      tv, img;

; image warped object on flat detector
        mag = (zd0 - zs) / (zo - zs);   Warped object to flat detector
        x1 = xs + mag * (xo - xs);
10      y1 = ys + mag * (yo - ys);
        ix = floor((x1 - xc0) / mag0 + n / 2);
        iy = floor((y1 - yc0) / mag0 + n / 2);
        img = bytarr(n, n);
        img[ix[ndx], iy[ndx]] = obj[ndx];
15      window, 4, xsize=n, ysize=n, title='Warped Obj/ Flat Det'
        tv, img;

; define warped detector pixel array
        zd = zd0 + mag * zo;
20      magw = (zd - zs) / (zo -zs);
        x2 = xs + magw * (xo - xs);
        y2 = ys + magw * (yo - ys);
        ix = floor((x2 - xc0) / mag0 + n / 2);
        iy = floor((y2 - yc0) / mag0 + n / 2);
25      img = bytarr(n, n);
        img[ix[ndx], iy[ndx]] = obj[ndx];
        window, 5, xsize=n, ysize=n, title='Warped Obj/Warped Det'
        tv, img;

30      end;
```

FIG. 8B

TOMOGRAPHY OF CURVED SURFACES

TECHNICAL FIELD

The subject matter disclosed here generally relates to reconstruction of curved surfaces, via tomography, and, more particularly, via X-ray tomosynthesis or laminography.

BACKGROUND

"Tomography," as used here, is a general term describing various techniques for imaging one or more cross-sectional "focal plane(s)" through an object. Tomography typically involves forming projections of a region of interest using some type of penetrating radiation, such as x-rays, sound waves, particle beams, or products of radioactive decay, that are then combined with the application of a reconstruction technique. Tomography has been applied in diverse fields to objects ranging in size from microscopic to astronomical. X-ray tomography, for example, is commonly used to inspect solder joints for defects formed during fabrication of printed circuit assemblies.

In "laminography," also known as "classical tomography," two or more of the source, object, and detector are moved in a coordinated fashion during exposure to produce an image of the desired plane on the detector. It is also possible to replace mechanical motion with electronic scanning (e.g. of the source or detector). The motion may be in a variety of patterns including, but not limited to, linear, circular, helical, elliptical, or random. In each case, the motion is coordinated so that the image of the focal plane remains stationary and in sharp focus on the detector, while planes above and below the focal plane move and are blurred into the background. Reconstruction takes place in the detector during exposure and consists simply of integration. Laminography can be considered a form of "dynamic tomography" since motion is typically continuous throughout exposure.

Like laminography, tomosynthesis requires coordinated positioning of the source, detector and object. In fact, similar data acquisition geometries may be used in each case. Tomosynsthesis differs from laminography in that projections are acquired with the motion stopped at multiple, fixed points. Reconstruction is then performed by digitally averaging, or otherwise combining, these projections.

Tomosynthesis can be considered a digital approximation to laminography, or a form of "static tomography," since the source and detector are typically stationary during each projection. However, this dichotomy between dynamic and static tomography is somewhat dated and artificial since numerous hybrid schemes are also possible. Tomosynthesis, which can also be considered a specific form of computed tomography, or "CT," was first described in D. Grant, "Tomosynthesis: A Three-Dimensional Radiographic Imaging Technique", IEEE Trans. Biomed. Eng: BME-19: 20–28, (1972), and incorporated by reference here.

In typical laminography, a single, flat focal plane is chosen in advance for imaging during an acquisition cycle. With tomosynthesis, on the other hand, a single set of projections may be used repeatedly to reconstruct images of focal planes at varying heights. This "tomosynthetic reconstruction" is typically accomplished by shifting or translating the projections relative to each other prior to combining.

A common problem for many types of tomography is that the region(s) of interest may not lie in a single, flat plane, and, indeed, may be arranged on one or more arbitrarily complex surfaces. For example, one may wish to image solder joints in a region of a printed circuit board which is warped or the complex articular surface of a biological joint in a medical application. Tomosynthetic reconstruction of tilted, flat planes is generally described in J. Liu, D. Nishimura, and A. Macovski, "Vessel Imaging Using Dual Energy Tomosynthesis", Med. Phys. 14(6): 950–955 (1987) and in Z. Kolitsi, G. Panayiotakis, V. Anastassopoulos, A. Scodras, and N. Pallikarakis, "A Multiple Projection Method for Digital Tomosynthesis," Med. Phys. 19(4): 1045–1050 (1992), which are both incorporated by reference here. However, these references do not consider the various problems associated with curved, or otherwise non-flat, focal planes such as warped printed circuit boards.

In some cases the acquisition geometry may be adapted to accomplish this for a particular application. For example, JP52030395 to Shoichi is incorporated by reference here and, according to an English-language abstract, discloses a curved tomography camera for panoramically photographing a specific curved dislocation region in a horizontal patient. The Shoichi drawings appear to illustrate a collimated x-ray source and a rotating detector moving in arcs that are concentric with the human ribcage being imaged. While well-suited for relatively simple shapes which are known in advance, such an approach appears to lack the flexibility to adapt to arbitrarily complex surfaces determined at run time.

With regard to dynamic tomography, U.S. Pat. No. 5,687,209 to Adams (assigned at issuance to Hewlett-Packard Co.) discloses a laminography system with automatic test object warp compensation and is also incorporated by reference here. The Adams laminography system uses two or more linear detectors and one or more collimated X-ray sources. Discrete X-ray images, with different viewing angles, are generated by each detector and then analyzed by a computer to generate Z-axis test object warp compensation parameters based upon the location of a pre-determined feature in a test object found in each image. The discrete X-ray images are then combined using these warp compensation parameters to generate laminographic images of different planes in the object under test.

However, the Adams technique uses features in each of several shadowgraph images to determine a two-dimensional shift distance for the entire image in the corresponding shadowgraph. The technique can therefore produce distorted reconstructions for a variety of reasons discussed in more detail below.

SUMMARY

These and other drawbacks of conventional technology are addressed here by providing a device for tomography of curved surfaces including a source of penetrating radiation; an object having a curved surface; and a detector having a curved shape corresponding to the curved surface. Also disclosed is a method for tomography of curved surfaces including the step of projecting energy through an object having a curved surface onto a detector having a curved shape corresponding to the curved surface.

In an exemplary embodiment, a method of tomography of a curved surface in an object is provided that includes determining an expected distortion for each of a plurality of points in a projection of the curved surface onto a detector; and correcting each of the plurality of points in the projection according to the expected distortion of that point by replacing pixel values in the uncorrected projection with corresponding interpolated pixel values at the expected positions.

BRIEF DESCRIPTION OF THE DRAWINGS

Various aspects of the invention will now be described with reference to the following figures ("FIGS.") which are not necessarily drawn to scale, but use the same reference numerals to designate corresponding parts throughout each of the several views.

FIGS. 8A and 8B are an input file for the IDL (Interactive Data Language) from Research Systems.

DETAILED DESCRIPTION OF THE PREFERRED EMBODIMENTS

Figure 1:
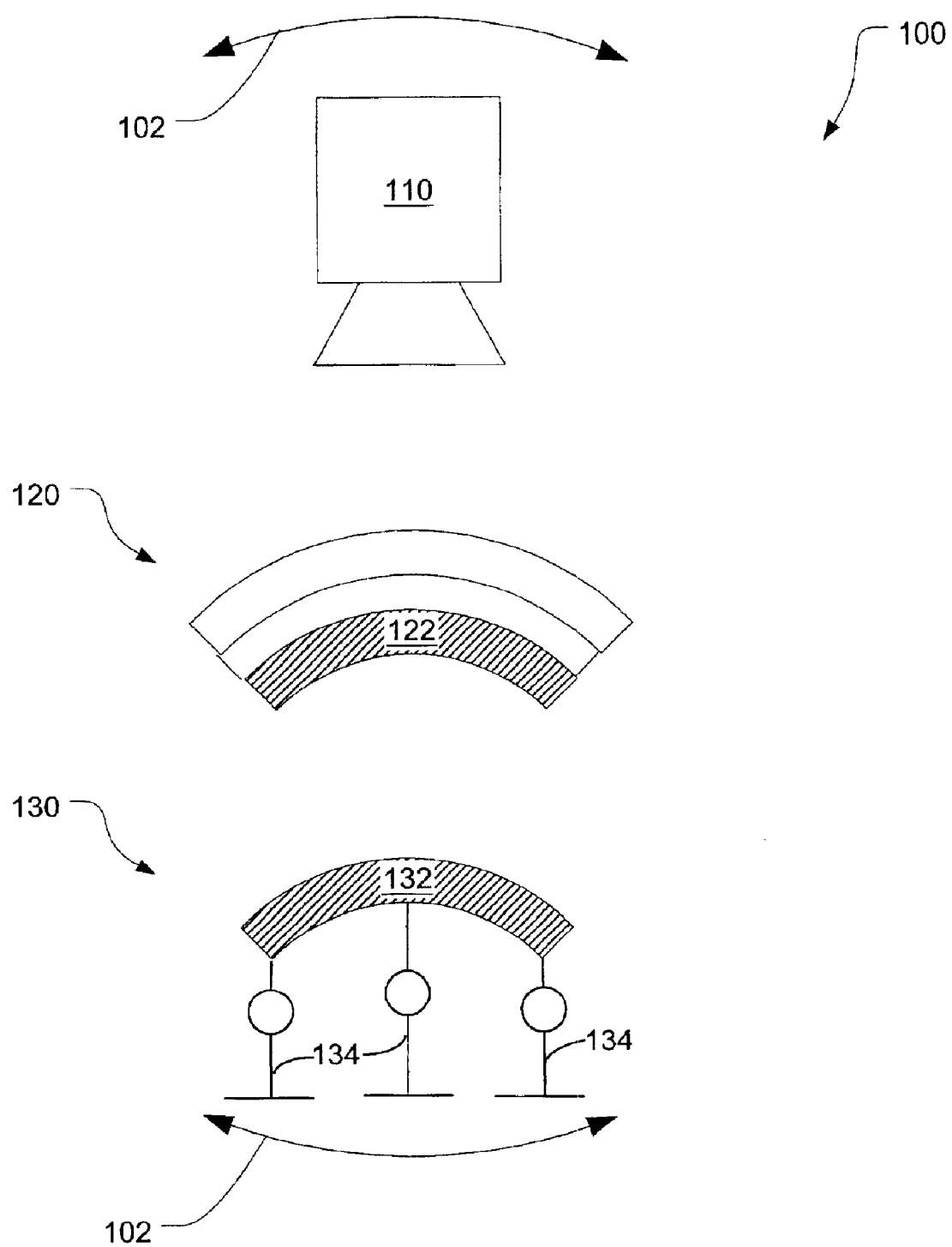
FIG. 1 is a cross-sectional schematic diagram of one embodiment of a system for tomography of curved surfaces.

FIG. 1 is a cross-sectional schematic diagram of one embodiment of a tomography system 100 for curved surfaces. The term "tomography" is used here to include both static and dynamic tomography. The tomography system 100 includes at least one source 110, an object 120, and a detector assembly 130. The arrows 102 illustrate that the source 110 and/or the detector assembly 130 are repositioned between each projection (for static tomography) or moved during image acquisition (for dynamic tomography). Alternatively, or in addition, the object 120 may also be moved during or between multiple acquisition cycles. Hybrid schemes in which motion occurs both between and during image acquisition are also possible.

The source 110 may be any conventional X-ray, or other suitable penetrating energy, source for passing energy through the object 120 to the detector assembly 130. The illustrated object 120 includes at least one curved, or otherwise non-flat, surface 122 that is under investigation as the desired focal surface. For example, the curved surface of interest 122 may be one side of a warped printed circuit board assembly having solder connections that must be non-destructively inspected. The curved surface of interest 122 for which a cross-sectional image is desired may also lie partly or entirely within the interior of object 120. Curved, or otherwise non-planar, cross-sections of a variety of other planar and/or non-planar features and/or objects may also be imaged with the tomography system 100 shown in FIG. 1.

The detector assembly 130 shown in FIG. 1 includes a curved, or otherwise non-planar, detector 132 for sensing and/or recording energy from the source 110 as it passes through the object 120. In particular the detector 132 has, or may be made to take on, a shape and orientation that corresponds to the shape of the curved surface 122 under investigation. For example, the detector 132 is preferably geometrically similar and has the same orientation to the surface of interest 122. The term "geometrically similar" is used here to refer to surfaces, or portions of surfaces, having corresponding shapes that are not necessarily the same size.

For example, the relative sizes of the detector 132 and surface of interest to 122 may be scaled in order to account for the overall magnifications of the system 100. This scale factor may also vary, for example, when the direction and desired focal surface have different orientations or shapes. For the sake of illustration, FIG. 1 shows only simple, convex curved surfaces 122 and 132. Arbitrarily complex curved surfaces may also be provided. However, each ray traced from the source 110 to the detector 132 should preferably intersect the surface of interest 122 in only a single point.

The tomography system 100 shown in FIG. 1 corrects in real time for magnification changes and image distortion caused by the shape and/or orientation of the desired focal section 122, permitting both dynamic and static tomography of curved (and/or otherwise non-planar) surfaces. However, changes in brightness may arise from several sources including some portions of the detector 132 being closer to the source 110 than other portions of the detector. Variations in orientation of the detector, the magnification, and the path length through the sample may also cause variations in brightness.

If desired, such brightness distortions may be compensated by varying the gain associated with the detector 132 in a pixel-by-pixel manner, either during readout or by post-processing the resulting images. Variations resulting from source-to-detector distance can be corrected using pixel gains which are a function of detector pixel height. Variations caused by changes in detector orientation can similarly be corrected with gains which vary as a function of the cosine of the angle between the local detector surface normal and a ray traced from the source. The latter correction is particularly applicable to individual projections obtained with static tomography. Nonetheless, it may also be applied to dynamic tomography either by varying the pixel gains during image acquisition, or, in an approximate fashion, by applying averaged correction factors to the final image.

Since pixel brightness is inversely proportional to magnification squared, correction to a standard magnification may also be performed. Changes in path length through the object causing brightness variations as a non-linear function of $\cos(\theta)$ and are generally more difficult to correct for. With monochromatic sources, a gain that is dependent on $\cos(\theta)$ can be applied after taking the logarithm of the fraction of intensity transmitted. However, such corrections are only approximate for broadband sources such as x-ray tubes. Consequently, in practice, such path length corrections are often ignored in tomosynthesis and laminography. The various correction factors discussed above are generally independent and may therefore be multiplied.

The detector 132 is preferably deformable so that it can be configured to correspond with curved surfaces 122 having arbitrary shapes and/or other curved focal planes. For example, the detector 132 may include flexible X-ray film or other deformable energy sensor, or an array of inflexible detectors arranged in a flexible substrate. In this regard, the detector assembly 130 may be further provided with optional actuators 134 for shaping the detector 132 to correspond with the curved surface 122 under investigation. For example, electromechanical servos may be used to adjust the relative height of various portions of the detector 132.

Figure 2A:
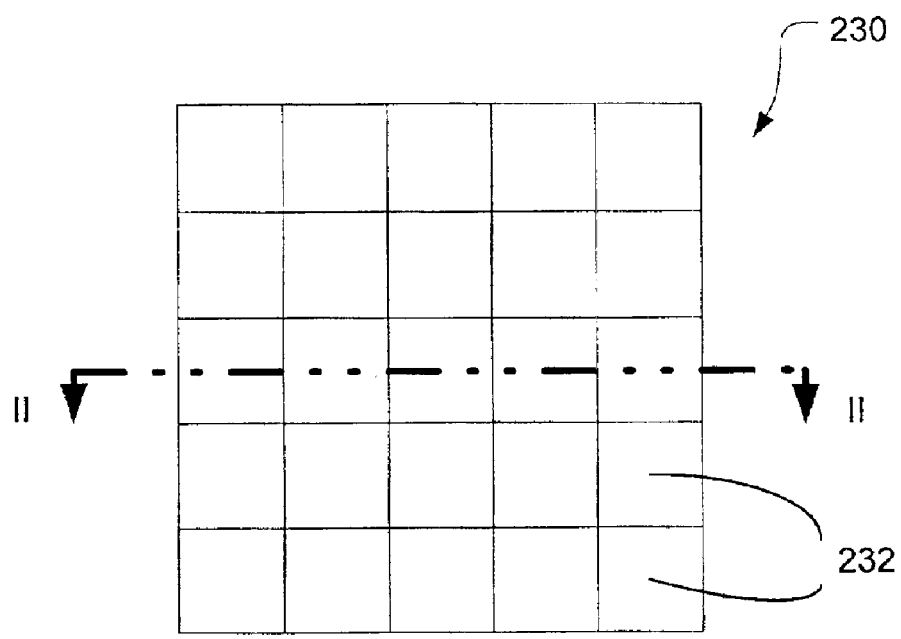
FIG. 2A is a top schematic view of a detector array for use with the tomography system shown in FIG. 1.
Figure 2B:
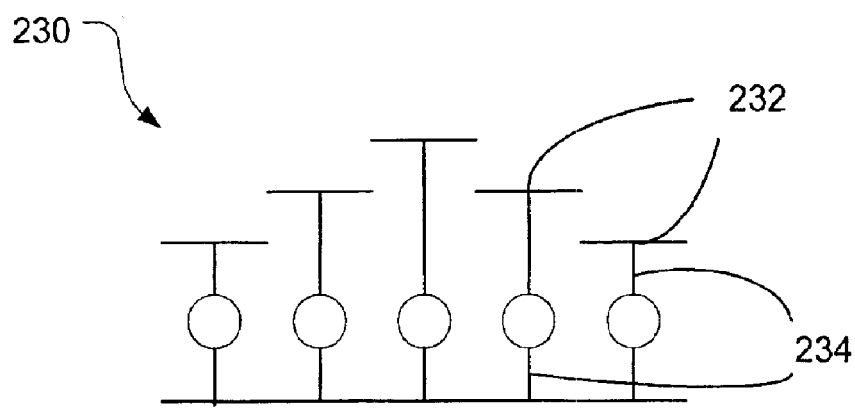
FIG. 2B is a cross-sectional view taken along section lines II—II in FIG. 2B.

FIGS. 2A and 2B illustrate an alternative detector array 230 having numerous small, closely-spaced, flat detectors 232. Each of the detectors 232 may record one or more pixels of the resulting image. Information from some, or all, of the detectors 232 may then be evaluated in order to limit the investigation to particular areas, such as the immediate vicinity of joints or other features under inspection. As best shown in FIG. 2B, each planar detector 232 in the detector array 230 may be provided with a vertical actuator 234. The actuators 234 may also be configured to provide additional degrees of translational and/or rotational freedom in order to provide further control of their surface orientation.

Figure 3:
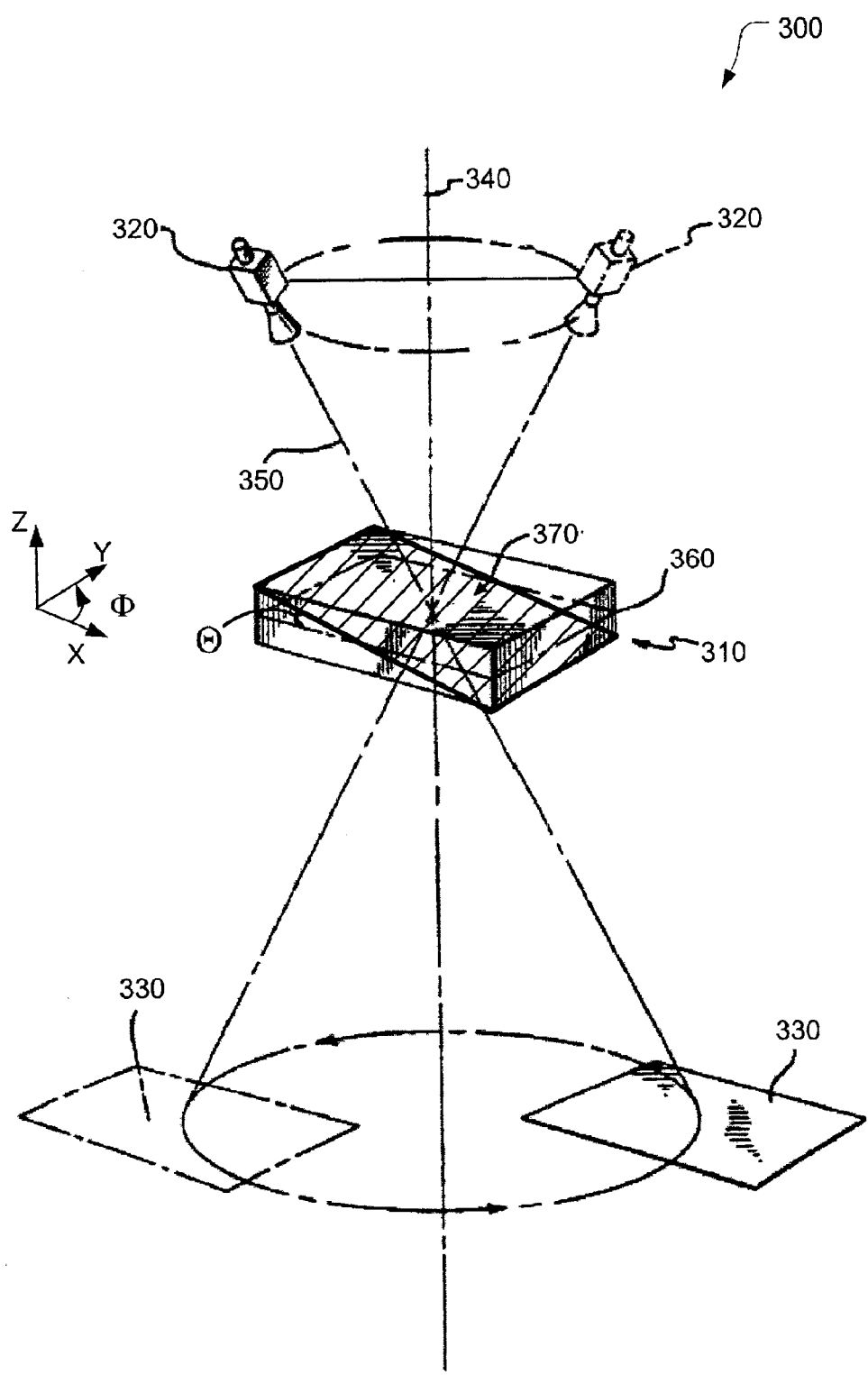
FIG. 3 is a schematic illustration of a typical data acquisition geometry for implementing the tomography system shown in FIG. 1.

FIG. 3 is a three-dimensional representation of one of many possible data acquisition geometries 300 for use with the tomography system 100 shown in FIG. 1 and/or other tomography systems. As in FIG. 1, the object 310 under examination (for example, a printed circuit board assembly) in this particular geometry 300 is held in a stationary position with respect to a source of X-rays 320 and an X-ray detector assembly 330. However, other configurations may also be used.

The detector assembly 330 may include various features of the detector assemblies 130 and 230 discussed above with regard to FIGS. 1 and 2. Synchronous rotation of the X-ray source 320 and detector 330 about a common axis 340 allows an X-ray image of the horizontal plane 360 within the object 310 to be formed on the detector 330. In FIG. 3, the detector 330 is illustrated as being planar and horizontal. However, the techniques described below may be extended to non-planar and/or non-horizontal detectors.

FIGS. 4A–4D illustrate several types of distortion that can arise when a surface is projected onto a geometrically dissimilar detector or one with a different orientation. FIGS. 4A–4D compare the results of projecting the horizontal reference plane 360 on the planar horizontal detector 330 against those obtained by projecting a plane 370 that is tilted at an angle $\Theta$ about the y-axis onto the same detector 330. More specifically, FIGS. 4A–4D illustrate a series of such projections where the diamonds represent points in a rectangular grid on the horizontal image plane 360, and the circles represent corresponding points on the tilted (non-horizontal) image plane 370.

The x-axis shown in FIG. 3 runs from left to right in the charts shown in FIGS. 4A–4D, while the y-axis runs from bottom to top. The origin (and axis of rotation) is coincident with the central circle in each of FIGS. 4A–4D. The angular position of the x-ray source, measured counter-clockwise from the x-axis, is denoted as in FIG. 3 so that FIGS. 4A–4D represent $\phi=0$, 90, 180, and 270°, respectively. Since rotation of the tilted plane 370 is about the y-axis, points from the tilted plane 370 along the y-axis remain in the focal plane and are represented by circles which are superimposed on the corresponding diamonds in each projection shown in FIGS. 4A through 4D. However, points on the tilted plane 370 which are to the left of the y-axis are above the horizontal focal plane 360, while those to the right of the y-axis are below the focal plane.

As illustrated by the circles in FIGS. 4A–4D, the position and magnification of points in the tilted plane 370 will be distorted in at least three ways. The first type of distortion is shortening by a factor of $\cos(\Theta)$ in a direction perpendicular to the axis about which the sample is rotated. However, since $\Theta$ is generally small, this so called "shortening distortion" in the x direction is typically minor. Consequently, this particular type of distortion does not appear as a striking difference between the circle and diamond projection patterns shown in FIGS. 4A–4D.

A second type of distortion is the "keystone distortion" that is caused by the difference in vertical height between corresponding points (diamonds) from the horizontal plane 360 and (circles) the tilted plane 370. Since the vertical source to detector distance between the source 320 and detector assembly 330 is fixed for this example, the magnification of the projected image is determined by the height from the horizontal plane 360 in the z-direction of each point on the tilted plane 370. These magnification differences manifest themselves in the generally trapezoidal outline of the circles forming projections from the tilted grid 370.

"Parallax distortion" causes points below and above the horizontal focal plane 360 to appear to shift toward and away from the direction of the source, respectively. This is the effect that is exploited in conventional laminography to cause blurring of the "out of focus" planes. For the tilted plane 370 shown in FIG. 3, parallax distortion leads to various image changes depending on the position of the source as described below.

Figure 4A:
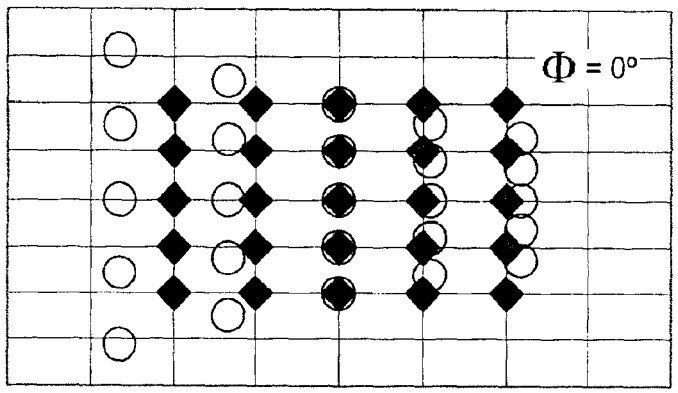
FIGS. 4A through 4D are schematic illustrations of projections made using the data acquisition geometry shown in FIG. 3.
Figure 4B:
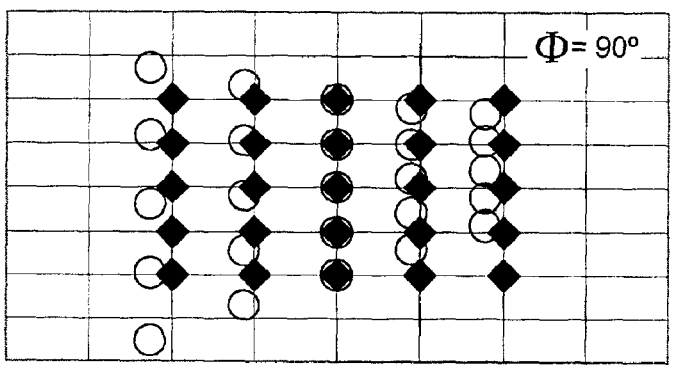
Figure 4C:
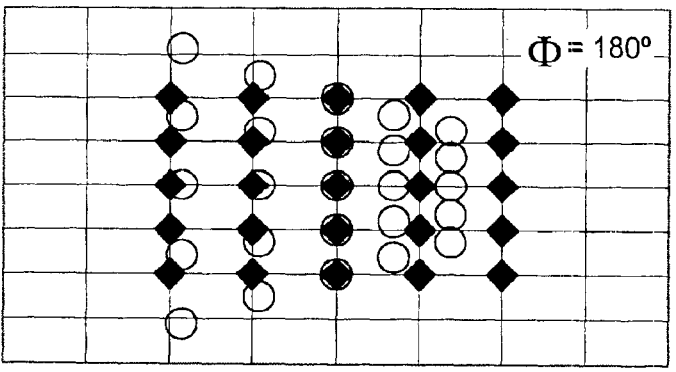
Figure 4D:
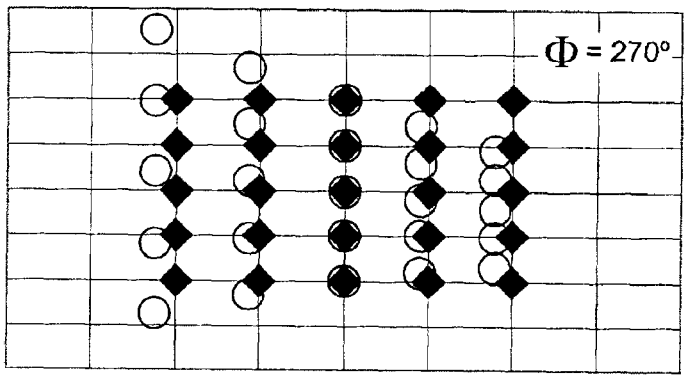

At $\phi=0°$ shown in FIG. 4A, parallax distortion leads to stretching of the image pattern in the x direction, while at $\phi=180°$ shown in FIG. 4C parallax distortion leads to compression in the x direction. Similarly, at $\phi=90°$ and $\phi=270°$ shown in FIGS. 4B and 4D, respectively, parallax distortion causes shearing of the projected image. In the former case, points to the right of the y-axis are shifted upward and those to the left are shifted downward. In the latter case, shearing in the opposite direction occurs.

Intermediate values of $\phi$ (not shown) yield additional combinations of shortening, stretching, compression, and/or shearing as a function of the displacement in the Z-direction from the horizontal plane 360. As a result, in this example of a flat, but tilted object plane 370, these distortions increase linearly with distance from the y-axis. Distortions for displacement along other axes may also be similarly predicted. In the general case, distortions do not vary linearly across the image but may still be predicted in a similar manner as discussed below.

FIGS. 4A–4D illustrate that once the position of the source 320, surface of interest 370, and detector 330 are known, as well as the shape and orientation of the surface of interest 370 and the detector 330, then the resulting projected image may be obtained by ray tracing and/or other techniques. Although ray tracing was used to produce the examples above, other factors, including source spot size, scatter, and/or detector resolution may also be included in more detailed models of the imaging system, if desired. In any event, ray tracing will generally provide a geometrically undistorted image when the surface of interest and detector have geometrically similar shapes and orientation, and are scaled to match the magnification of the imaging chain. Hence, if the detector has, or can be made to take on, the desired shape and orientation, undistorted images can be obtained using either static or dynamic tomography as discussed above with regard to FIG. 1.

Alternatively, in static tomography, one can use any detector shape and orientation and then digitally correct any resulting distortions in the individual projections prior to reconstruction. For example, when the map from the undistorted projection to the distorted projection is one-to-one and invertible, then the distortion may be corrected in each projection, and the image restored, pixel-by-pixel, to that which would have been obtained had the surface and detector possessed a geometrically similar shape and orientation. A computationally efficient and effective method for correcting geometric distortions is described in L. Yaroslavsky, "Advanced Image Processing Lab," European Signal Processing Conference 2000, (Tampere, Finland, Sep. 4, 2000) and L. Yaroslavsky and M. Eden, "Fundamentals of Digital Opticals," (Birkhauser, Boston 1996), which are both incorporated by reference here in their entirety.

By zooming in, i.e. increasing the number of pixels, it is possible to obtain an almost continuous approximation to the distorted image. Distortion correction with good preservation of image quality can then be achieved by transferring the pixel values from the predicted location in the zoomed, distorted images to the corresponding location in the corrected image. Sinc interpolation is a preferred method for zooming in on the distorted projections, but other methods may also be used. For example, efficient sinc interpolation using zero padding and FFT algorithms or their "pruned" variants are described in T. Smith, M. Smith, S. Nichols "Efficient Sinc Function Interpolation Technique For Center Padded Data", IEEE Trans. Acoust. Speech Signal Proc. 38:1512–1517 (1990) and in J. Markel, "FFT Pruning", IEEE Trans. Audio Electron. AU-19: 305–311, (1971), which are each incorporated by reference here. Alternatively, or in addition, sinc interpolation may be performed using the methods described in Yaroslavsky, "Efficient Algorithm for Discrete Sinc Interpolation," Applied Optics, 36(2): 460–463 (1997), which is also incorporated by reference here and is advantageous in terms of accuracy, flexibility, and computational complexity.

Once the corrections have been completed for each projection, then the corrected projections can be recombined using conventional tomosynthesis or other reconstruction techniques. When using tomosynthetic reconstruction, the corrected projections may also be shifted in order to reconstruct any member of a family of similar curved surfaces at differing z-axis heights. However, unlike in conventional tomosynthesis, surfaces at different heights may also be corrected for changes in magnification and/or partially corrected for associated, secondary changes in brightness using the techniques described here.

Various aspects of a system for tomosynthetic imaging of arbitrarily curved and/or titled surfaces will now be described in more detail with respect to FIGS. 3 and 5–11. In the following discussion, the source 320 in FIG. 3 will be defined to be located at z=+z. Similarly, the location of the ideal, horizontal focal plane 360 will be defined at z=0, and the detector 330 at $z=-z_D$. The desired focal surface 370 can then be described parametrically, or otherwise, as a function z=g(x, y). Typically, the desired focal surface 370 will have a mean near z=0, although this is not strictly required. For simplicity, the following description also presumes projection geometries leading to common projection magnification, "$M_O$," and common resolutions, with undistorted and aligned imaging of the horizontal planes. However, a variety of other similar methods may be construed from the present disclosure for other configurations and/or assumptions.

Figure 5:
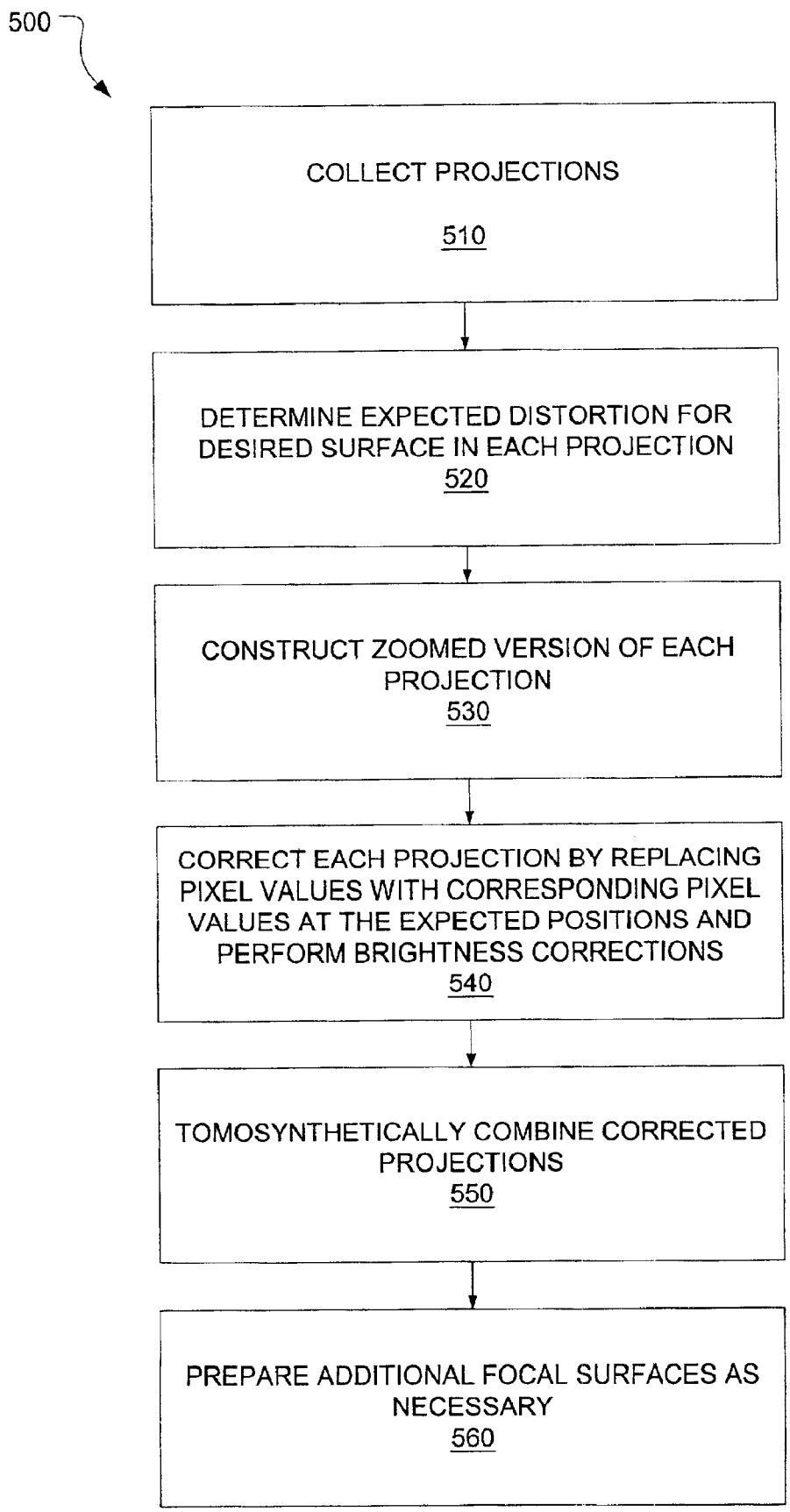
FIG. 5 is a flowchart for a tomography method using the principles illustrated in FIGS. 4A–4D.
Figure 6:
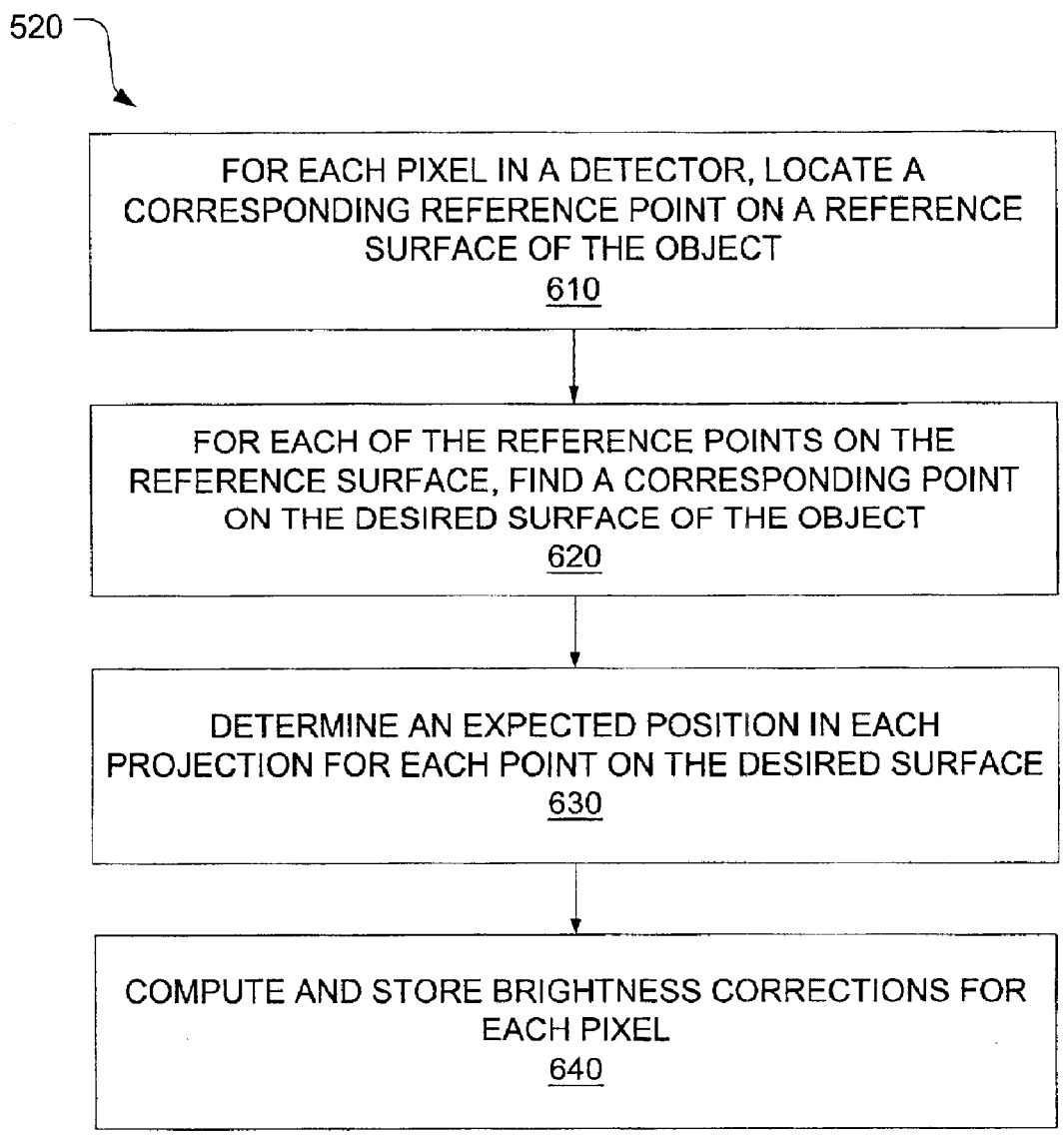
FIG. 6 is a flowchart showing one of the steps in FIG. 5 in more detail.
Figure 7:
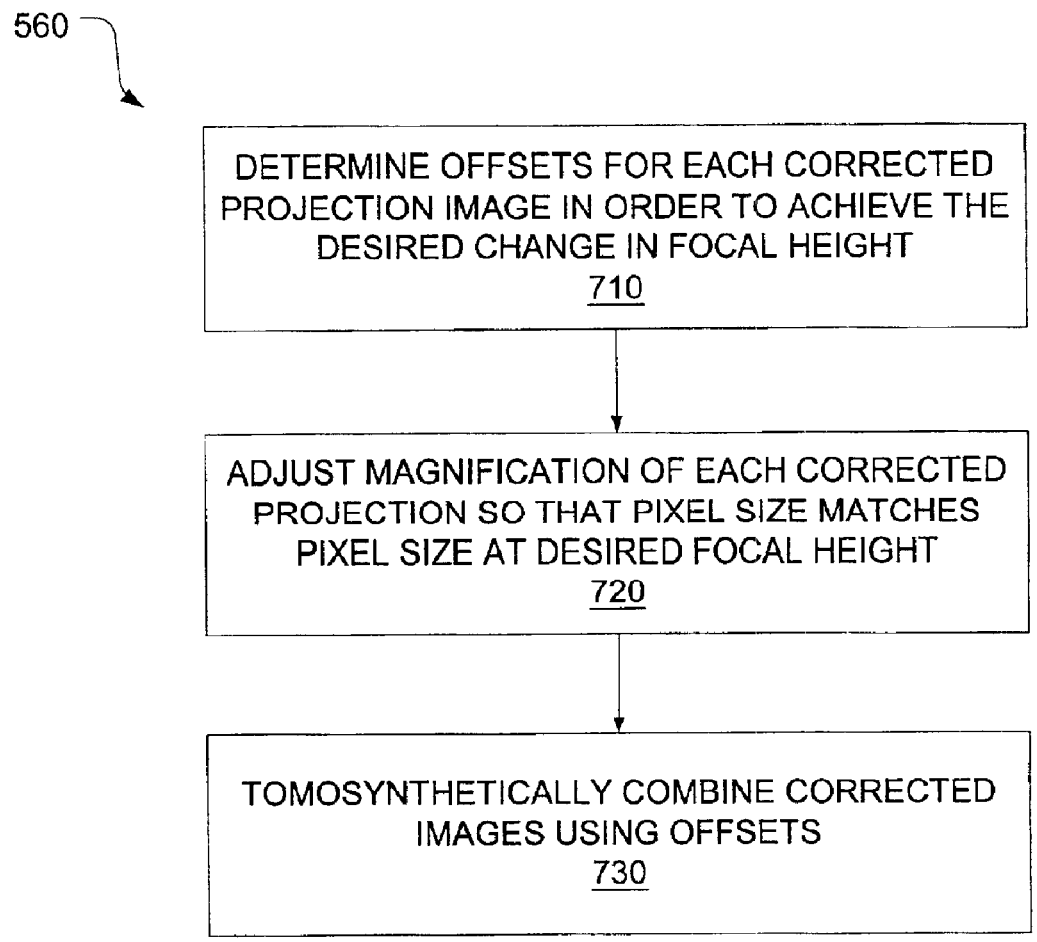
FIG. 7 is a flowchart showing another one of the steps in FIG. 5 in more detail.

FIGS. 5–7 show the architecture, functionality, and operation of a tomography method 500 that may be implemented with the device shown in FIG. 3, and/or other devices, where the desired focal surface 370 may be tilted, curved, or otherwise non-flat. Each block in FIGS. 5–7 represents an activity, step, module, segment, or portion of computer code that will typically comprise one or more executable instructions for implementing the specified logical function(s). However, a variety of other computer, electrical, electronic, mechanical, and/or manual systems may also be similarly configured to operate in a similar manner.

It should also be noted that, in various alternative implementations, the functions noted in the blocks will occur in an order different than noted in figures. For example, multiple functions in different blocks may be executed substantially concurrently, in a different order, incompletely, and/or over an extended period of time, depending upon the functionality involved. Various steps may also be completed manually.

The tomography method 500 begins with the collection of projection views at step 510. Except as noted, the processing of individual views described below may occur in parallel or may be overlapped with collection of other projections. At step 520, the expected distortion for each projection of the desired surface 370 is computed. The position of the desired focal surface 370 relative to the reference surface 360 will typically have been previously determined or inferred, for example by laser surface mapping and/or other techniques. Although, horizontal reference surface 360 is illustrated in FIG. 3, non-horizontal and/or curved reference surfaces may also be used, as may curved detector assemblies 130, 230 shown in FIGS. 1 and 2.

Various aspects of step 520 are shown in more detail in FIG. 6. At step 610, a series of hypothetical points, $\{x_i, y_i\}$, corresponding to each detector pixel are placed in the x-y reference plane 360 (FIG. 3), where z=0. These points are preferably arranged in a regular grid so that each point projects to the center of the corresponding detector pixel by ray tracing. However, other arrangements may also be used.

At step 620, the corresponding point on the curved focal plane 370 $\{z_i=g(x_i, y_i)\}$ is found by, for example, projection along the z axis. Then, at step 630, the projected position corresponding to each point $\{x_i, y_i, z_i\}$ in the distorted image is computed using, for example, ray tracing. Finally, brightness corrections are computed at step 640. For example, a ratio comparing the magnification in the distorted image relative to the ideal image ($M/M_0$) may be stored for each point, as described above.

Returning to FIG. 5, a zoomed version of the previously-collected projected image is created at step 530. The minimum required zoom factor may be chosen based on the high frequency content of the projection. A linear zoom factor of 2–8 (or 4–64X in area) may also be chosen empirically or otherwise. At step 540, the corrected projection image is constructed by replacing the pixel value in the original image by the pixel value at the corresponding position in the zoomed projection. Corrections to brightness may also be imposed at this stage. The zoomed projection is no longer required after step 540 is complete, and may therefore be discarded.

At step 550, the corrected projections are tomosynthetically combined to form an image of the selected focal surface. For example, tomosynthesis may be carried out using pixel averaging or order statistics (e.g. min, max, or nth brightest or darkest at a particular pixel location). Additional focal surfaces above or below the tomosynthetic image may also be constructed at step 560.

Various details of step 560 are illustrated in FIG. 7. At step 710, the shifts, or "offsets," in the x and y directions that are required for each projection in order to achieve the desired change in focal height are determined. If desired, the magnification may also be corrected at step 720 to match that which would have been obtained at the ideal focal height using sinc interpolation. Typically, a different number of pixels than was originally obtained will result from this operation. However, the resulting pixel size will match that at the ideal focal height. Finally, similar to step 550 (FIG. 5), the corrected images are tomosynthetically combined using the offsets and magnifications from steps 710 and 720.

As noted above, the tomography method 500 shown in FIGS. 5–7 may be implemented in a wide variety of electrical, electronic, computer, mechanical, manual, and/or other configurations. However, in a typical embodiment, the system 500 will be at least partially computerized with various aspects of the system being implemented by software, firmware, hardware, or a combination thereof. When the tomography system 500 is at least partially implemented in hardware, the system may be implemented using a variety of technologies including, but not limited to, discrete logic circuit(s) having logic gates for implementing logic functions upon data signals, application specific integrated circuit(s), "ASIC(s)", having appropriate combinational logic gates, programmable gate array(s), "PGAs", and/or field programmable gate array(s), "FPGAs." When implemented in software, the tomography system 500 may be part of a source program (or "source code"), executable program ("object code"), script, or any other entity comprising a set of instructions to be performed as described in more detail below. Such software may be written using an object oriented programming language having classes of data and methods, and/or a procedure programming language, having routines, subroutines, and/or functions. For example, suitable programming languages include, but are not limited to, C, C++, Pascal, Basic, Fortran, Cobol, Perl, Java, and Ada.

Such software may be stored on any computer readable medium for use by, or in connection with, any computer-related system or method. For example, the computer readable medium may include any electronic, magnetic, optical, or other physical device or means that can contain or store a computer program for use by, or in connection with, a computer-related system or method. The computer-related system may be any instruction execution system, apparatus, or device, such as a computer-based system, processor-containing system, or other system that can fetch the instructions from the instruction execution system, apparatus, or device and then execute those instructions. Computer-readable medium therefore includes any means that will store, communicate, propagate, or transport the program for use by, or in connection with, the instruction execution system, apparatus, or device.

For example, the computer readable medium may take a variety of forms including, but is not limited to, an electronic, magnetic, optical, electromagnetic, infrared, or semiconductor system, apparatus, device, or propagation medium. More specific examples of a computer-readable medium include, but are not limited to, an electrical connection (electronic) having one or more wires, a portable computer diskette (magnetic), a random access memory ("RAM") (electronic), a read-only memory ("ROM") (electronic), an erasable programmable read-only memory ("EPROM," "EEPROM," or Flash memory) (electronic), an optical fiber (optical), and a portable compact disc read-only memory ("CDROM") (optical). The computer readable medium could even be paper or another suitable medium upon which the program is printed, as the program can be electronically captured, for instance via optical sensing or scanning of the paper, and then compiled, interpreted or otherwise processed in a suitable manner before being stored in a memory.

In a typical embodiment, once the hardware and/or software implementation of the tomography system illustrated in FIGS. 3–7 is accessed, a processor will typically be configured to execute instructions corresponding to the method 500 (FIGS. 5–7) in conjunction with an operating system stored within a memory. The processor will also receive and execute further instructions and data stored in memory or made available from various input/output devices (such as the source and/or detector assemblies discussed above) so as to generally operate the system pursuant to the instructions and data contained in the software and/or hardware.

Figure 9:
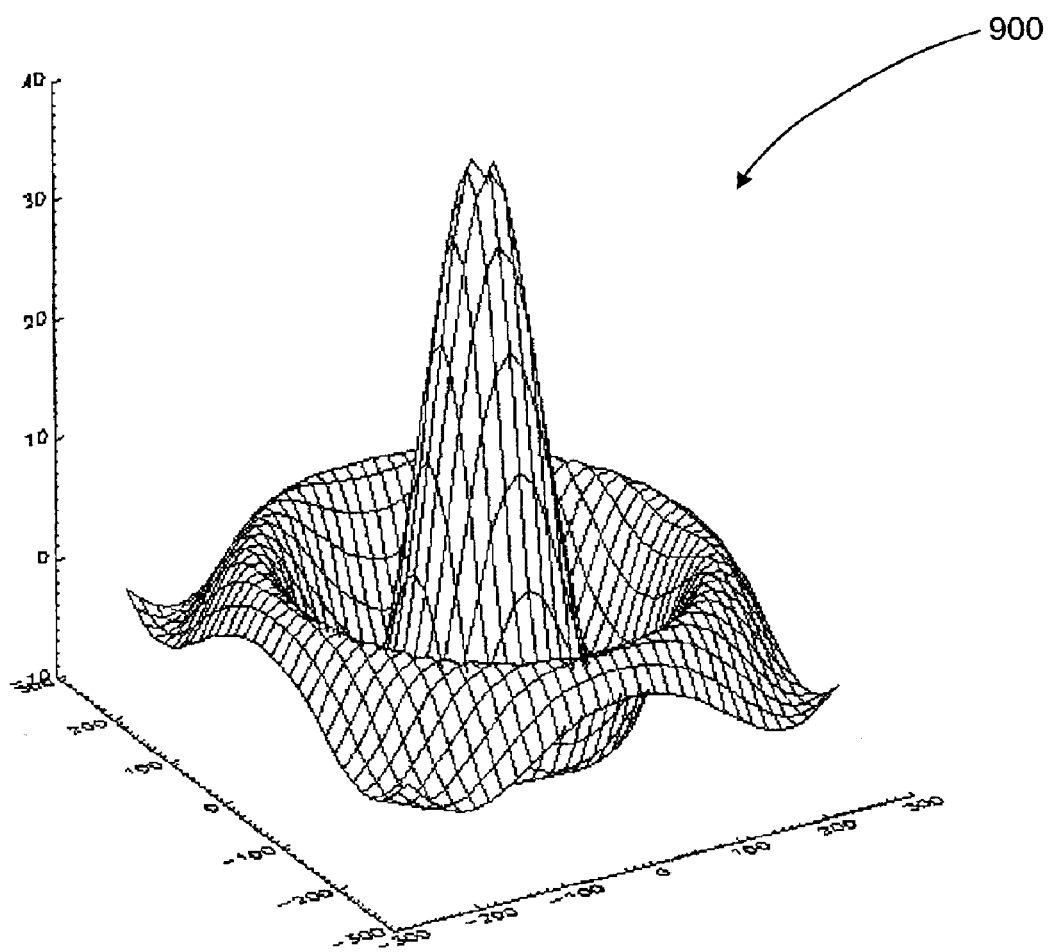
FIG. 9 is a mesh representation of a curved surface obtained from using the input file in FIGS. 8A and 8B.

FIGS. 8–11 refer to a computer simulation illustrating various aspects of the embodiments described above. For simplicity, this code is written using nearest neighbor interpolation without zooming instead of sync interpolation. More specifically, FIGS. 8A–8B show an input file for IDL (Interactive Data Language) from Research Systems. In FIG. 8A, line 4 specifies the sizes of the images shown in FIGS. 9–11, 256×256 pixel in this case. Lines 6–10 provide height values for the curved surface 900 shown in FIG. 9. Although the particular "Mexican Hat" function shown in FIG. 9 is $z=\sin(r)/r$, a variety of other functions could be used to simulate other curved surfaces.

Lines 14–20 in FIG. 8A define a reference, rectangular grid of pixel elements positioned at $x=x_0$, $y=y_0$ and $z=0$ with element (0,0) at the center of the grid. The pixel values of the reference object, "obj" are then initialized to zero except on a 15×15 set of gridlines which are set to 255. Lines 27–39 then plot a mesh representation of the curved or "warped" surface defined at lines 6–10. Lines 41–43 similarly display the flat reference surface defined by "obj." Lines 45–48 in FIG. 8A define the position of a source used in subsequent ray tracing calculations.

Figure 10:
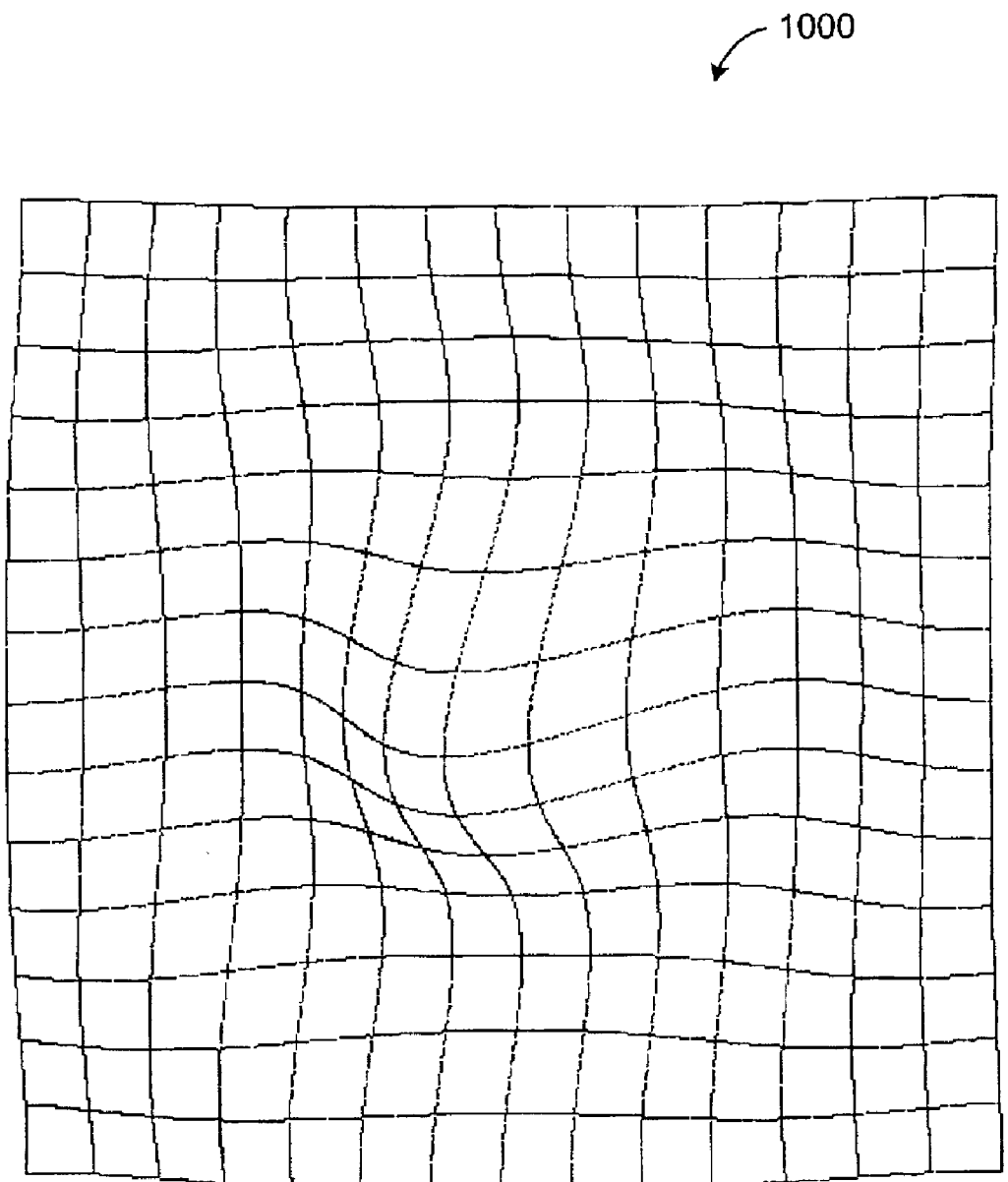
FIG. 10 is a mesh representation of the curved surface in FIG. 9 projected onto a flat surface using the input file shown in FIGS. 8A and 8B.
Figure 11:
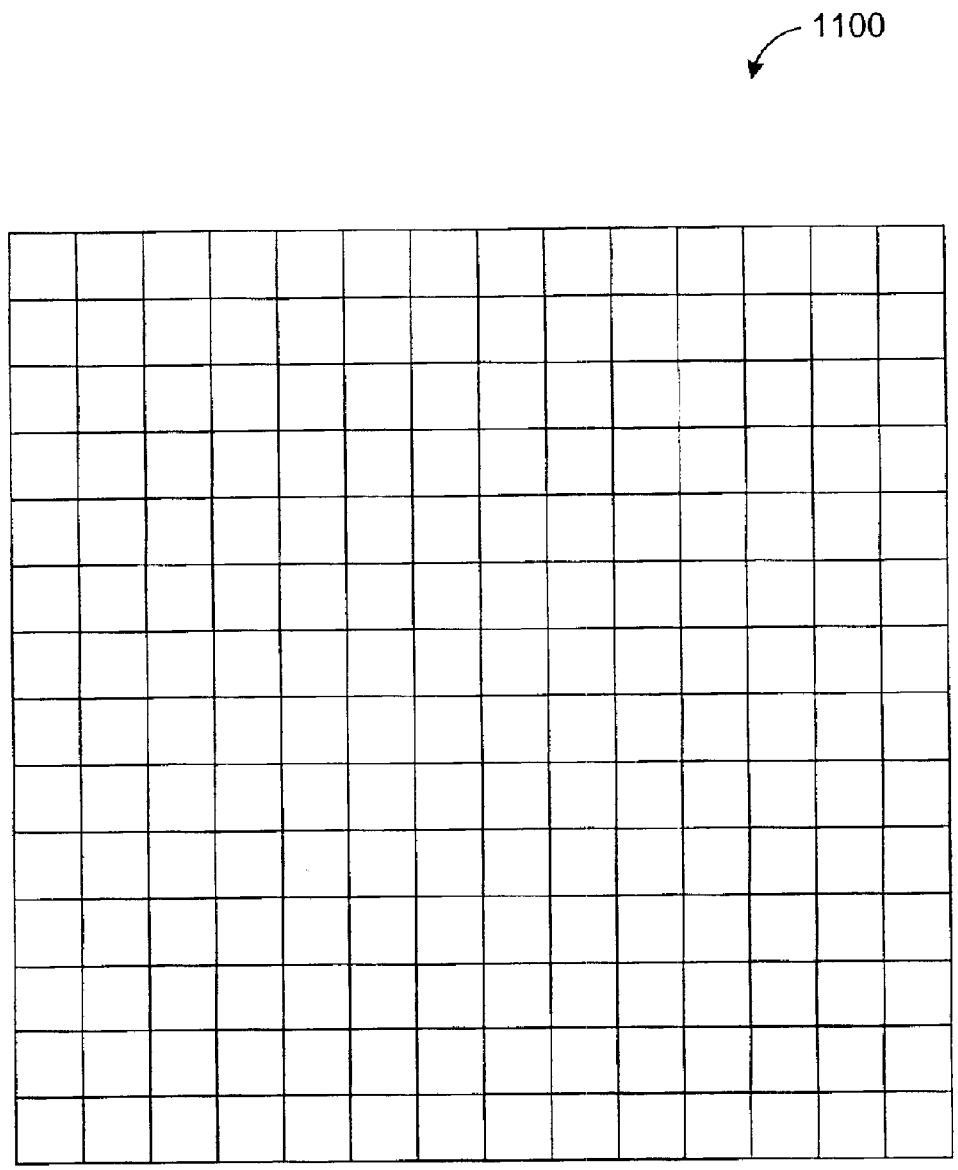
FIG. 11 is a mesh representation of the image in FIG. 10 that has been corrected for distortion using the input file in FIGS. 8A and 8B.

Lines 50–57 of FIG. 8A and lines 1–3 in FIG. 8B perform ray tracing calculations for imaging the flat reference surface stored in "obj" onto a flat, rectangular grid. These ray tracing calculations are then displayed, resulting in an undistorted grid. Lines 7–14 in FIG. 8B perform similar ray tracing for the curved surface shown in FIG. 9 onto a flat detector. The results of those calculations are shown in the distorted image 1000 shown in FIG. 10. Lines 18–28 in FIG. 8B go on to perform ray tracing onto a curved detector having a shape and orientation corresponding to the curved surface 900 and to plot the results as shown in FIG. 11.

It will be noted that an undistorted image of the curved surface 900 shown in FIG. 9 can be created (FIG. 11) using a detector having a shape and orientation corresponding to that of the curved surface under investigation. FIG. 10, on the other hand, illustrates that it is possible to predict the distorted image 1000 that is produced on a flat detector by a curved surface 900 when the shape of the curved surface is known. For example, the distortion in an image produced from a warped printed circuit can be similarly predicted once the warp curvature is measured or otherwise determined. Furthermore, using the techniques described above with regard to FIGS. 5–7, the distorted image shown in FIG. 10 can be corrected to the undistorted condition shown in FIG. 11.

It should be emphasized that the embodiments described above, and particularly any "preferred" embodiments, are merely examples of various implementations that have been set forth here to provide a clear understanding of various aspects of the invention. One of ordinary skill will be able to alter many of these embodiments without substantially departing from scope of protection defined solely by the proper construction of the following claims.

What is claimed is:

1. A device for tomography of an object having a curved surface comprising:
   a source of penetrating radiation;
   a detector having a curved shape corresponding to the curved surface; and
   a processor system configured to determine an expected distortion for each of a plurality of points in a projection of the curved surface onto the detector, and configured to correct each of the plurality of points in the protection according to the expected distortion of that point by replacing pixel values in the uncorrected projection with corresponding interpolated pixel values at the expected positions.

2. The device recited in claim 1, wherein said detector is deformable.

3. The device recited in claim 2, further comprising at least one actuator for shaping the deformable detector.

4. The device recited in claim 1, wherein said detector further comprises a plurality of spaced, flat detector elements.

5. The device recited in claim 4, further comprising a plurality of actuators wherein each actuator positions at least one of the detectors according to the shape of the curved surface.

6. A method for tomography of a curved surface in an object, comprising the steps of:
   determining an expected distortion for each of a plurality of points in a projection of the curved surface onto a detector; and
   correcting each of the plurality of points in the protection according to the expected distortion of that point by replacing pixel values in the uncorrected projection with corresponding interpolated pixel values at the expected positions.

7. The method recited in claim 6, further comprising the step of projecting energy through the object having the curved surface onto the detector having a curved shape corresponding to the curved surface.

8. The method recited in claim 7, further comprising the step of forming the detector into the curved shape.

9. The method recited in claim 7, further comprising the step of correcting the detected energy levels for brightness distortions.

10. The method recited in claim 6, wherein said determining step further comprises the steps of:
    for each of the points in the projection, locating a corresponding reference point on a reference surface of the object;
    for each of the reference points on the reference surface, finding a corresponding point on the curved surface of the object; and
    determining an expected distortion in the projection for each point on the curved surface.

11. The method recited in claim 6, further comprising the steps of:
    repeating the determining and correcting steps for a plurality of projections; and
    reconstructively combining the corrected projections.

12. The method recited in claim 6, wherein the detector is curved.

13. The method recited in claim 6, wherein the reference surface is curved.

14. A device for tomography of a curved surface in an object, comprising:
    means for determining an expected distortion of a plurality of points in a projection of the curved surface on a detector; and
    means for correcting the projection according to the expected distortion of at least two of the points; and
    means for replacing pixel values in the uncorrected projection with corresponding pixel values at corrected positions.

15. The device recited in claim 14, wherein the determining means further comprises:
    means for designating a reference surface in the object, said reference surface having a shape corresponding to a surface of the detector;
    means for determining a deviation from the reference surface for each of a plurality of points on the curved surface; and
    means for determining an expected distortion in the projection for each of the points based upon the determined deviation from the reference surface.

16. The device recited in claim 15, further comprising:
    means for repeating the determining and correcting steps for a plurality of projections; and
    means for reconstructively combining the corrected projections.

17. The device recited in claim 16, wherein said combining means further comprises:
    means for determining an offset for each of the corrected projections; and
    means for tomosynthetically combining the adjusted and corrected projections using the determined offsets.

18. The device as recited in claim 17, wherein said combining further comprise means for adjusting a brightness of each corrected projection.

19. The device recited in claim 14, wherein the reference surface is curved.

20. A method for tomography of a curved surface in an object, comprising the steps of:
    determining an expected distortion for each of a plurality of points in a projection of the curved surface onto a detector; and
    correcting each of the plurality of points in the projection according to the expected distortion of that point, wherein said determining step further comprises the steps of:
       for each of the points in the projection, locating a corresponding reference point on a reference surface of the object;
       for each of the reference points on the reference surface, finding a corresponding point on the curved surface of the object; and
       determining an expected distortion in the projection for each point on the curved surface.

21. The method recited in claim 20, wherein the correcting step includes the step of replacing pixel values in the uncorrected projection with corresponding interpolated pixel values at expected positions.

22. The method recited in claim 20, further comprising the step of forming the detector into the curved surface.

23. The method recited in claim 20, further comprising the step of correcting the detected energy levels for brightness distortions.

24. The method recited in claim 20, further comprising the steps of: repeating the determining and correcting steps for a plurality of projections; and reconstructively combining the corrected projections.

25. A device for tomography of a curved surface in an object, comprising:

means for determining an expected distortion of a plurality of points in a projection of the curved surface on a detector; and means for correcting the projection according to the expected distortion of at least two of the points, wherein the determining means further comprises:

means for designating a reference surface in the object, said reference surface having a shape corresponding to a surface of the detector;

means for determining a deviation from the reference surface for each of the plurality of points on the curved surface; and means for determining the expected distortion in the projection for each of the points based upon the determined deviation from the reference surface.

26. The device recited in claim 25, further comprising means for replacing pixel values in the uncorrected projection with corresponding pixel values at corrected positions.

27. The device recited in claim 25, further comprising:

means for repeating the determining and correcting steps for a plurality of projections; and means for reconstructively combining the corrected projections.

28. The device recited in claim 27, wherein said combining means further comprises:

means for determining an offset for each of the corrected projections; and means for tomosynthetically combining the adjusted and corrected projections using the determined offsets.

29. The device recited in claim 25, further comprising means for deforming the surface of the detector to correspond with the reference surface in the object.

30. The device recited in claim 25, further comprising means for correcting detected energy levels for brightness distortions.

31. The device recited in claim 30, wherein the detector further comprises a deforming detector that is deformed to correspond with the curved surface of the object.

32. A device for tomography of an object having a curved surface comprising:

a source of penetrating radiation;

a detector having a curved shape corresponding to the curved surface; and a processor system configured to determine an expected distortion for each of a plurality of points in a projection of the curved surface onto the detector, and configured to correct each of the plurality of points in the projection according to the expected distortion of that point by locating a corresponding reference point on a reference surface of the object for each of the points in the projection, by finding a corresponding point on the curved surface of the object for each of the corresponding reference points on the reference surface, and by determining the expected distortion in the projection for each point on the curved surface.

33. A computer-readable medium having a program for tomography of a curved surface in an object, the program comprising logic configured to perform the steps of:

determining an expected distortion of a plurality of points in a projection of the curved surface on a detector; and correcting the projection according to the expected distortion of at least two of the points, wherein the determining further comprises:

designating a reference surface in the object, said reference surface having a shape corresponding to a surface of the detector;

determining a deviation from the reference surface for each of the plurality of points on the curved surface; and determining the expected distortion in the projection for each of the points based upon the determined deviation from the reference surface.

34. A computer-readable medium having a program for tomography of a curved surface in an object, the program comprising logic configured to perform the steps of:

determining an expected distortion for each of a plurality of points in a projection of the curved surface onto a detector; and correcting each of the plurality of points in the projection according to the expected distortion of that point by replacing pixel values in the uncorrected projection with corresponding interpolated pixel values at expected positions.

* * * * *